United States Patent
Teeslink et al.

(10) Patent No.: US 9,259,212 B2
(45) Date of Patent: *Feb. 16, 2016

(54) VASCULAR WOUND CLOSING APPARATUS AND METHOD

(71) Applicant: Wound Care 360, LLC, Olathe, KS (US)

(72) Inventors: Charles Rex Teeslink, Augusta, GA (US); Griscom Bettle, Sarasota, FL (US)

(73) Assignee: Wound Care 360, LLC, Olathe, KS (US)

( * ) Notice: Subject to any disclaimer, the term of this patent is extended or adjusted under 35 U.S.C. 154(b) by 204 days.

This patent is subject to a terminal disclaimer.

(21) Appl. No.: 13/803,759

(22) Filed: Mar. 14, 2013

(65) Prior Publication Data
US 2014/0031861 A1 Jan. 30, 2014

Related U.S. Application Data

(60) Provisional application No. 61/696,871, filed on Sep. 5, 2012, provisional application No. 61/674,905, filed on Jul. 24, 2012.

(51) Int. Cl.
*A61B 17/00* (2006.01)
*A61B 17/132* (2006.01)

(52) U.S. Cl.
CPC .......... *A61B 17/0057* (2013.01); *A61B 17/132* (2013.01); *A61B 17/1325* (2013.01); *A61B 2017/00659* (2013.01)

(58) Field of Classification Search
CPC ............. A61B 17/132; A61B 17/1325; A61B 17/0057; A61B 2017/00659
USPC ................. 606/201, 213, 216, 217, 215, 218; 604/174, 177, 178, 179, 398; 602/75; 24/579.09
See application file for complete search history.

(56) References Cited

U.S. PATENT DOCUMENTS 4,773,421 A 9/1988 Davis
5,127,412 A 7/1992 Cosmetto et al.
(Continued)

FOREIGN PATENT DOCUMENTS

WO WO 2010/118312 A2 10/2010

OTHER PUBLICATIONS

Chen et al. "Vascular Closure Device-related Complications After Percutaneous Coronary Intervention." J Taiwan Cardiovasc Interv (2010) 1:24-27.
(Continued)

*Primary Examiner* — Melanie Tyson
*Assistant Examiner* — Mikail Mannan
(74) *Attorney, Agent, or Firm* — Hovey Williams LLP

(57) ABSTRACT

Wound closure apparatus is provided having a force-transmitting surface operable to be placed in a proximal, external, wound-closing position on a patient, together with a force-exerting assembly operable to exert a wound-closing pressure against the patient's tissue. The force-transmitting surface is preferably three-dimensionally asymmetric to generate different forces along the length of the surface. The apparatus is especially designed for the closure of wounds attendant to endovascular interventions, e.g., a femoral artery puncture wound. The apparatus is positioned and operated so as to partially close the patient's artery upstream of the arteriotomy. The apparatus and methods hereof may also be used for the closure of wounds created during venous intervention procedures. A smaller wound closure apparatus is provided for the closure of brachial and radial wounds, and has a wrist or arm strap for securing the apparatus onto the wrist or bicep region of a patient.

15 Claims, 6 Drawing Sheets

(56) References Cited

U.S. PATENT DOCUMENTS

| | | | |
|---|---|---|---|
| 5,263,965 A | 11/1993 | Roth | |
| 5,307,811 A | 5/1994 | Sigwart et al. | |
| 5,342,388 A | 8/1994 | Toller | |
| 5,690,610 A | 11/1997 | Ito et al. | |
| 5,690,674 A | 11/1997 | Diaz | |
| 5,728,120 A | 3/1998 | Shani et al. | |
| 5,746,755 A | 5/1998 | Wood et al. | |
| 5,792,173 A | 8/1998 | Breen et al. | |
| 5,919,207 A | 7/1999 | Taheri et al. | |
| 5,964,782 A | 10/1999 | Lafontaine et al. | |
| 6,074,356 A * | 6/2000 | Starkey et al. | 602/75 |
| 6,187,347 B1 | 2/2001 | Patterson et al. | |
| 6,264,673 B1 | 7/2001 | Egnelov et al. | |
| 6,331,182 B1 | 12/2001 | Tiefenbrun et al. | |
| 6,368,334 B1 | 4/2002 | Sauer | |
| 6,471,715 B1 | 10/2002 | Weiss | |
| 6,752,810 B1 | 6/2004 | Gao et al. | |
| 6,752,820 B1 * | 6/2004 | Hafemann | 606/203 |
| 7,081,124 B2 | 7/2006 | Sancoff et al. | |
| 7,087,060 B2 | 8/2006 | Clark | |
| 7,175,646 B2 | 2/2007 | Brenneman et al. | |
| 7,637,921 B2 | 12/2009 | Åkerfeldt et al. | |
| 7,780,612 B2 | 8/2010 | Ross | |
| 8,034,009 B2 | 10/2011 | Bates et al. | |
| 8,277,483 B2 * | 10/2012 | Teeslink et al. | 606/215 |
| 8,353,929 B2 * | 1/2013 | Teeslink et al. | 606/215 |
| 2003/0028214 A1 | 2/2003 | Benz et al. | |
| 2003/0163160 A1 | 8/2003 | O'Malley et al. | |
| 2004/0098034 A1 | 5/2004 | O'Connor | |
| 2004/0143289 A1 | 7/2004 | Zahler et al. | |
| 2004/0162577 A1 | 8/2004 | Tarone | |
| 2004/0267309 A1 | 12/2004 | Garvin | |
| 2006/0064124 A1 | 3/2006 | Zhu et al. | |
| 2006/0089667 A1 | 4/2006 | Ben-David | |
| 2006/0229662 A1 | 10/2006 | Finkielsztein et al. | |
| 2006/0229663 A1 | 10/2006 | Chiu et al. | |
| 2009/0082790 A1 | 3/2009 | Shad et al. | |
| 2009/0281569 A1 | 11/2009 | AlGhamdi | |
| 2010/0280541 A1 * | 11/2010 | Lampropoulos et al. | 606/203 |
| 2010/0286726 A1 | 11/2010 | Chalfoun et al. | |
| 2011/0152889 A1 | 6/2011 | Ashland | |
| 2011/0196417 A1 | 8/2011 | Clark | |
| 2011/0202089 A1 * | 8/2011 | Sun | 606/201 |
| 2011/0245868 A1 | 10/2011 | Teeslink et al. | |

OTHER PUBLICATIONS

Dauerman et al. (Vascular Closure Devices: The Second Decade J Am Coll Cardioll (2007) 50:17, 1617-1626 (Downloaded From: http://content.onlinejacc.org/ on Nov. 8, 2013).

International Search Report and Written Opinion dated Jul. 25, 2012, in related PCT Application No. PCT/US2012/022486 filed Jan. 25, 2012.

International Search Report and Written Opinion dated Aug. 10, 2013, in corresponding PCT Application No. PCT/US2013/050239 filed Jul. 12, 2013.

Office Action dated Jun. 21, 2012, in U.S. Appl. No. 13/421,253, filed Mar. 15, 2012.

Amendment dated Jul. 17, 2012, in U.S. Appl. No. 13/421,253, filed Mar. 15, 2012.

Supplemental Amendment dated Jul. 17, 2012, in U.S. Appl. No. 13/421,253, filed Mar. 15, 2012.

Examiner's Interview Summary dated Jul. 20, 2012, in U.S. Appl. No. 13/421,253, filed Mar. 15, 2012.

Second Supplemental Amendment dated Aug. 22, 2012, in U.S. Appl. No. 13/421,253, filed Mar. 15, 2012.

Notice of Allowance dated Aug. 28, 2012, in U.S. Appl. No. 13/421,253, filed Mar. 15, 2012.

Notice of Allowance dated Dec. 10, 2012, in U.S. Appl. No. 13/551,699, filed Jul. 18, 2012.

* cited by examiner

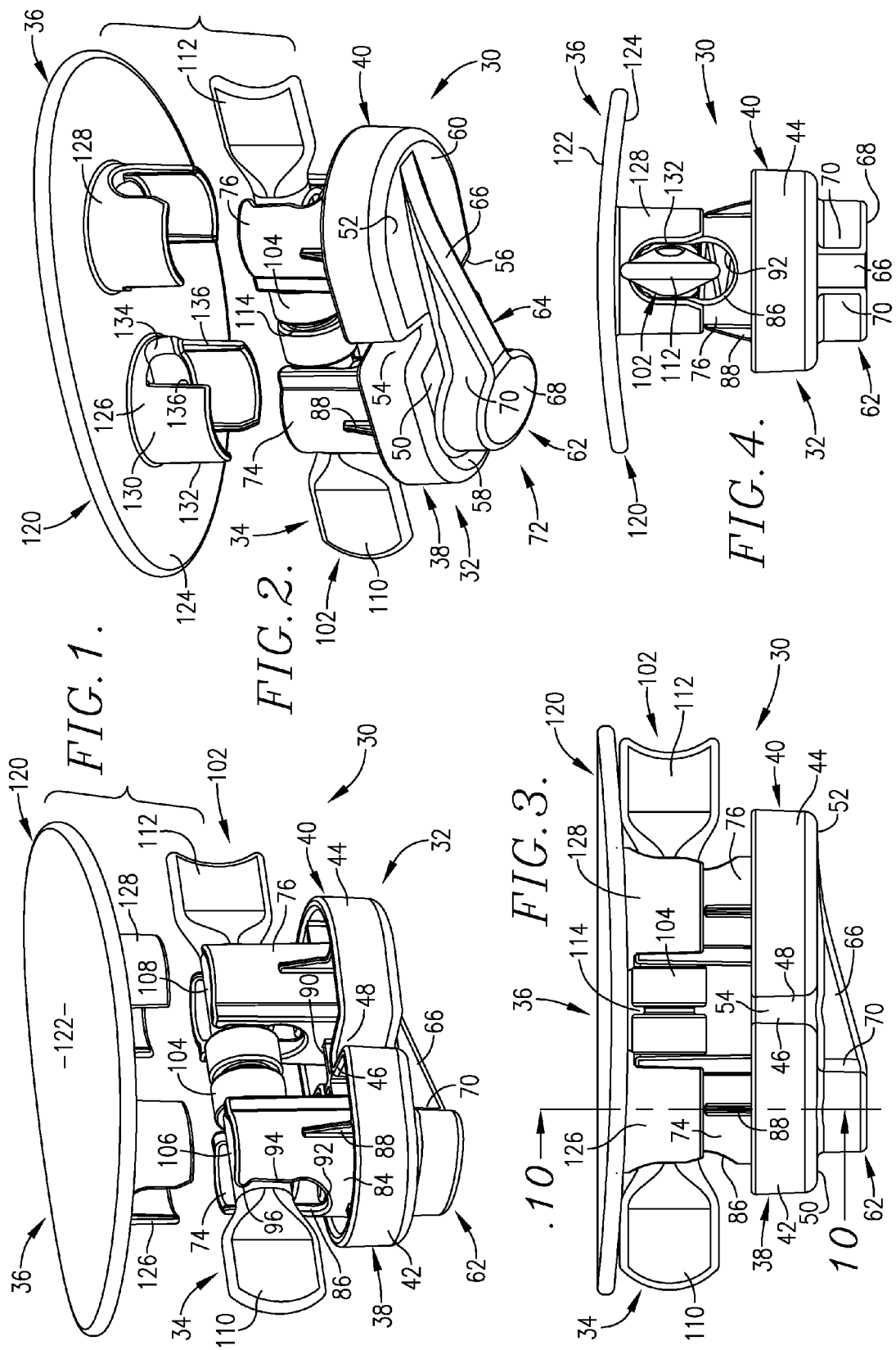

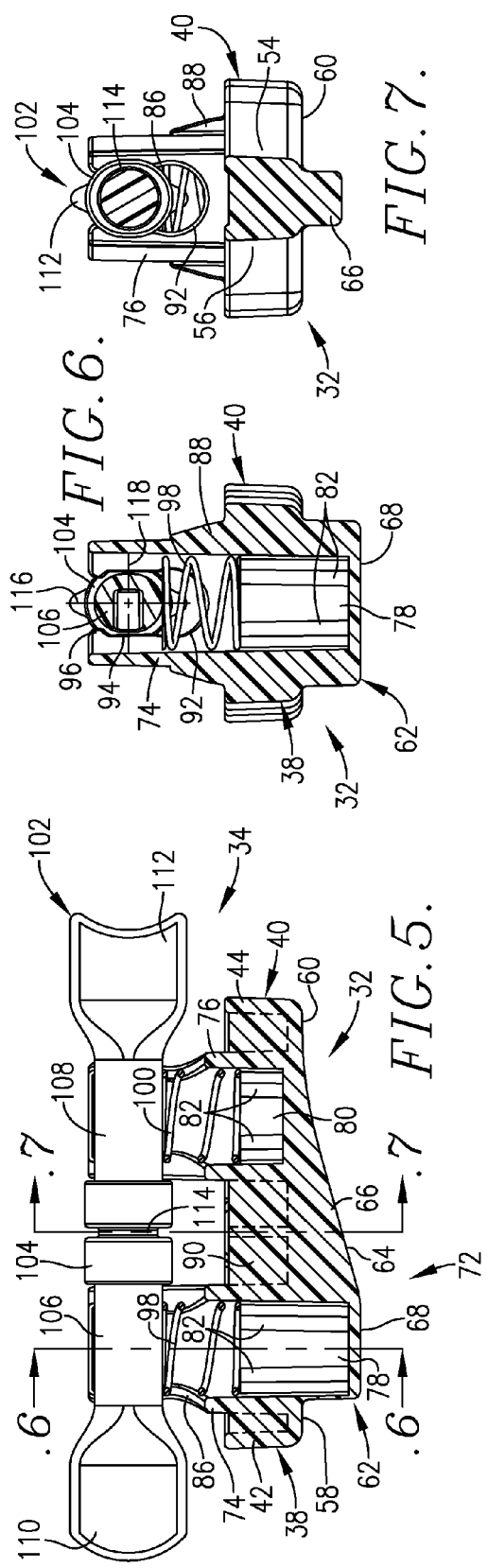

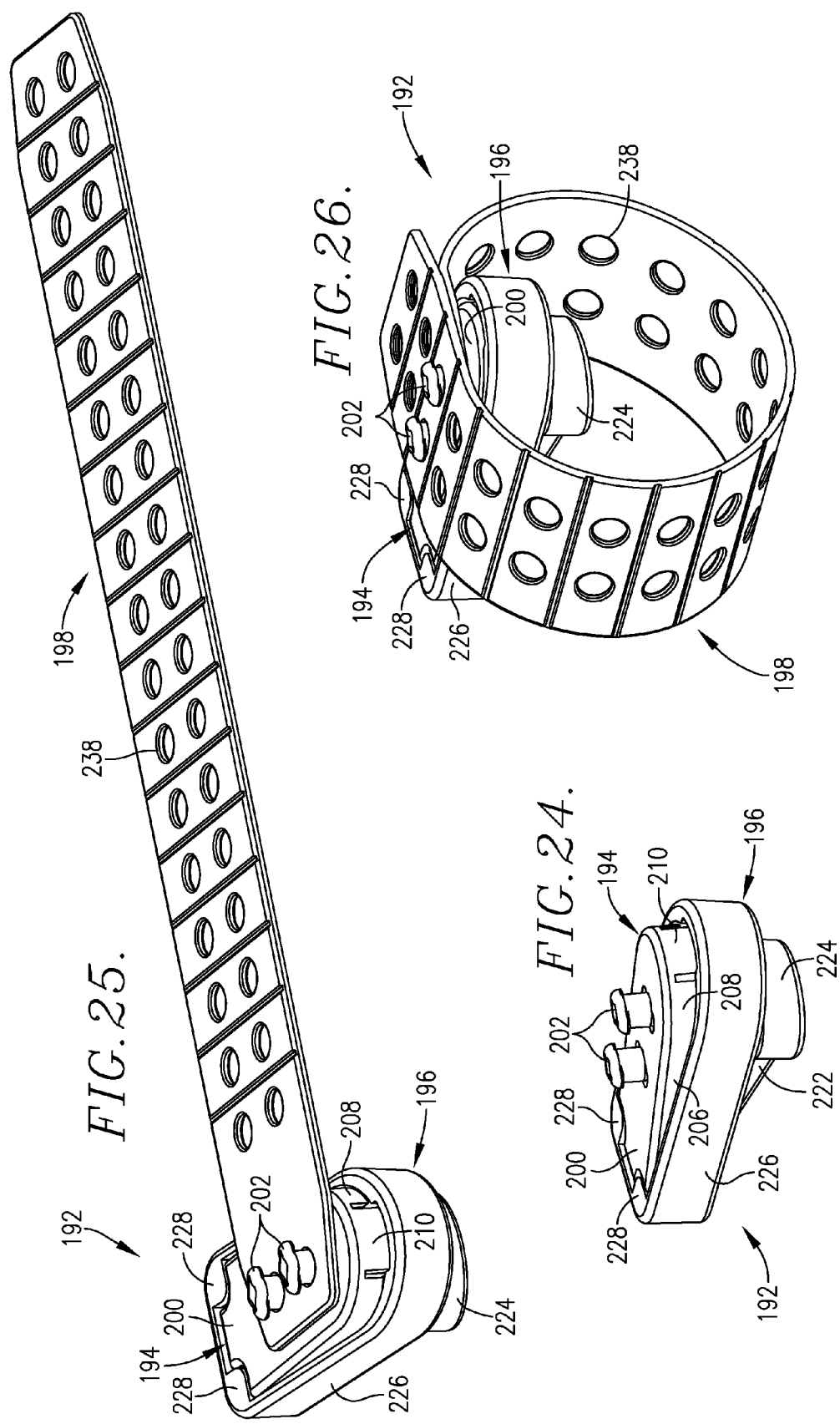

VASCULAR WOUND CLOSING APPARATUS AND METHOD

CROSS-REFERENCE TO RELATED APPLICATION

This application claims the benefit of Provisional Application Ser. No. 61/674,905, filed Jul. 24, 2012, and Provisional Application Ser. No. 61/696,871, filed Sep. 5, 2012.

BACKGROUND OF THE INVENTION

1. Field of the Invention

The present invention is broadly concerned with improved apparatus and methods for closure of wounds in the tissue of patients, and especially wounds attendant to endovascular interventions, such as percutaneous cardiac intervention (PCI) wherein closure is defined as the time from removal of the catheter to ambulating the patient. More particularly, the invention is concerned with such apparatus and methods which employs a wound-closing body placed adjacent and along the length of the wound, together with a force-exerting assembly operable to create forces which generate relatively high pressures on the patient's skin and tissue adjacent the wound. In preferred forms, the body has a three-dimensionally asymmetric lower force-transmitting surface so as to exert forces of different magnitudes at different locations along the force-transmitting surface. Also, the force-transmitting surface is preferably exerted substantially constantly and in a substantially time-invariant manner. In different embodiments, wound closure devices may be provided for femoral wound closure, or radial or brachial wound closure.

2. Description of the Prior Art

Endovascular interventions such as PCI are widely accepted as a practical treatment option for coronary artery disease. For example, femoral artery puncture is commonly used in endovascular diagnostic and interventional procedures. Alternately, access may be made via the radial or brachial artery. Such procedures are now commonly performed on an out-patient basis. In the case of a femoral arterial intervention, a puncture wound is made with a cannula to create an oblique subcutaneous tract and a terminal arteriotomy, followed by placement of a sheath within the tract. A catheter is then threaded through the sheath and into the adjacent artery, so that access can be had to the coronary arteries. After the diagnosis or intervention is completed, the catheter is withdrawn, the sheath is removed, and steps must be taken to close the wound. Wound closure typically involves compression to control bleeding until hemostasis occurs. Ideally, wound closure serves to minimize blood loss, effect hemostasis, and render the patient ambulatory in a relatively short period of time.

Poorly executed wound closures may give rise to complications which are costly, increase hospital stays and affect morbidity. For example, inadequate hemostasis can lead to significant blood loss, patient discomfort, vessel occlusion, thrombosis, formation of arteriovenous fistula, and pseudoaneurysm requiring surgical intervention and/or steps to avoid infections. Complications at the access site due to arterial cannulation occur in 1%-5% of cases, but may be as high as 14% with some interventional procedures.

Traditionally, wound closure has been a manual operation where a physician or nurse used manual hand pressure, using either one or two hands. One-handed manual pressure is usually carried out over a period of 30 minutes with a time to ambulation (TTA) of 4-6 hours. Two-handed manual pressure (often referred to as the "gold standard" of wound closure) ideally achieves optimal wound closure. In this technique, the healthcare professional's left hand exerts a semi-occlusive pressure upstream (closer to the heart) of the arteriotomy to moderate blood pressure fluctuations and to reduce the mean blood pressure from the heart without denying blood flow downstream. The professional's right hand holds an occlusive pressure over the arteriotomy, tract, and insertion site. This is continued for a period of approximately 30 minutes. However, in actual practice, there are a number of significant problems. For example, manual pressure that is too firm does not allow sufficient clotting factors to accumulate at the arteriotomy. Moreover, manual pressure along the tract varies because the tips of the four fingers of the right hand are not flat. Even more important, the person exerting manual pressure can tire during the 30-minute holding time, or the fingers may move or may not be placed properly. The person may also temporarily stop the application of pressure to examine the wound, causing a disruption of the maturing clot. Finally, different body types present different manual pressure issues, e.g., if the panniculus intrudes on the person's left hand, pressure variations may be induced as the patient breathes and the panniculus moves. TTA for this two-handed procedure is again normally 4-6 hours.

Manual techniques can be supplemented with use of applied hemostasis adjuncts, which reduce the time to hemostasis (TTH) to 5-6 minutes, but do not lower TTA because there is no force on the arteriotomy after hemostasis is achieved. Manual pressure may also be supplemented with external devices, such as C-clamps or sand bags. These combined techniques have many of the same problems as straightforward manual pressure closures, and the external devices may be difficult to deploy on obese patients. Thus, while manual procedures are of long standing, they are deficient in that they can be tiring, require careful training, and represent inefficient use of the time of valuable medical personnel.

Other closure techniques involve use of an intra-arterial anchor giving a TTH of about five minutes and a TTA of about 2-3 hours. Drawbacks of these procedures include a maximum French size of 8 Fr and the fact that the anchor and collagen plug must be left in the body for up to 90 days. Suture-mediated intra-arterial anchor techniques have also been used, but these are deficient in that the sutures remain in the body until absorbed, and nonetheless require that the anchor and plug be left in the body for an extended period. Finally, intra-tract closure has been used where the arteriotomy is mechanically stretched and then "boomerangs" back to an 18-gauge needle diameter. In these procedures, a heparin-neutralizing drug is deployed within the wound tract, and manual pressure is still required to close the 18-gauge needle hole.

In recent years, new, larger interventional devices of up to 20 Fr are being used to perform tasks like operations within the heart itself. No existing closure device is indicated for these large interventions, and resort must be had to manual pressure or surgical techniques to close the large wounds.

In response to these problems, various specialized vascular closure devices (VCDs) have been proposed, such as the device disclosed in U.S. Pat. No. 5,307,811 and commercialized under the designation "FemoStop." While these and other VCDs have achieved widespread use, no prior VCD has fully solved the problems inherent in wound closures. Dauerman et al. (*J AM COLL CARDIOLL.* 2007; 50 (17) Elsevier Science)—"Vascular Closure Devices: The Second Decade" described an ideal VCD:

The patient factors influencing closure success notwithstanding the "ideal" closure device remains to be developed. What would this device look like? 1) A single device capable of providing successful closure for all patient and success site anatomical variations; 2) an atraumatic device without a foreign body or vascular alteration of the femoral artery; and 3) a simple-to-use device with >95% procedural success and low cost.

The prior art uses the terms "pressure" and "force" loosely. A person exerting force through small fingers would apply more pressure than a person exerting the same force with larger fingers. A further complication is that the heart is beating, making the pressure (sum of internal and external pressure) variable. What is critical is controlling blood flow. If there were no flow restriction, the arteriotomy would leak, resulting in a hematoma. If there were complete flow restriction, then the downstream extremities would be starved of oxygen and the arteriotomy would be starved of necessary clotting factors. Hence, the ideal VCD is one in which flow is restricted, but not excessively.

Accordingly, there is an unfulfilled need in the art for a simple-to-use VCD which closely mimics "gold standard" manual wound closure, has a complication rate of <1%, can be used on all types of patients, gives very low TTH and TTA values, and does not involve residual drugs, sutures, or anchoring devices.

SUMMARY OF THE INVENTION

The present invention overcomes the problems outlined above and provides VCDs and corresponding methods which have many outstanding features. For example, preferred embodiments of the invention used in the context of femoral arterial PCI procedures are characterized by:

- a TTA on the order of 60 minutes for diagnostic PCI procedures;
- a complication rate of <1%;
- atraumatic, essentially painless wound closure with no residual foreign materials in the wound or vascular alterations;
- targeted asymmetric tissue pressures, with a larger non-occlusive pressure applied upstream of the arteriotomy to lower the patient's blood flow, with decreasing pressures downstream of the arteriotomy;
- substantially time-invariant wound closure pressures on the tissue;
- skin inversion adjacent the wound by means of a Z-stitch suture together with a rigid, force-transmitting surface including a transverse section positioned above the arteriotomy and generating force of greater than about 20 lbs., but not greater than the suture-rupturing force, and an obliquely oriented, axially extending section, which generates decreasing pressures downstream of the arteriotomy;
- secondary wound closure force through use of an adhesive sheet stretched over the device and adhered to the patient's skin on either side of the site;
- virtually no blood loss during wound closure;
- different sheath sizes, blood chemistries (e.g., INR>1.5, or the presence of blood thinners), and degrees of intervention can be accommodated by increasing the closure time;
- a device cost on the order of $100;
- wound closure procedure is typically learned with less than ten diagnostic procedures.

Many of these attributes are also useful in the context of radial or brachial wound closures at the bicep or wrist areas of patients. Hence, while short TTA's and sutures are not generally relevant in these contexts, the remainder of the factors listed above are normally important.

In the ensuing description, the methods and apparatus of the invention are described with particular reference to wounds incident to an arterial intervention procedures, such as femoral, radial, and brachial procedures. However, it should be understood that the invention is equally applicable to other types of vascular vessel procedures where a wound includes an opening in a non-arterial vascular vessel, such as a venous vessel.

In one aspect of the invention, apparatus is provided to close a wound in a patient's tissue where the wound presents an insertion site and an elongated, obliquely oriented tract extending into the patient's tissue and in communication with the insertion site. Such apparatus comprises a body having an elongated, force-transmitting surface and operable to be placed in an external wound-closing position with the force-transmitting surface proximal to the patient's skin, adjacent the wound and in general axial alignment with the tract. A force-exerting assembly is coupled with the body and is operable to exert forces of different magnitudes at different locations along the length of the force-transmitting surface in order to close the wound. In preferred forms, the force-transmitting surface is three-dimensionally asymmetric, and comprises first and second, preferably coplanar, surface sections having different force-transmitting areas respectively. Also, a third force-transmitting surface is provided which bridges the first and second surface sections and is generally T-shaped in configuration, presenting an elongated segment and a segment transverse to the elongated segment. Desirably, the elongated segment is obliquely oriented relative to the first and second surface sections.

The overall force-exerting assembly may also include structure for securing the body to the patient's tissue, and a mechanism including a shiftable component for generating a mechanically-derived force through the force-transmitting surface. In the context of femoral arterial wound closures, the securement structure preferably comprises a suture passing through the patient's tissue and tied to the body to hold the body in the wound-closing position. The suture may be in the form of a known Z-stitch suture which serves to invert the patient's skin at the wound site. The mechanism is preferably in the form of a biasing structure including at least one (and more preferably two) spring(s). Secondary forces may be generated by means of an adhesive sheet stretched over the device and adhered to the patient's skin on opposite sides of the wound site.

In the case of radial or brachial wound closing apparatus, the securement structure is preferably in the form of a compression strap, which may be passed around the wrist or bicep region of a patient to hold the apparatus in place during wound closure.

Advantageously, the force-exerting assembly is designed to exert a substantially constant and time-invariant force through the force-transmitting surface; this, coupled with the preferred asymmetric force application serves to reduce the patient's blood pressure and flow within the artery and especially at the arteriotomy.

BRIEF DESCRIPTION OF THE DRAWINGS

FIG. 1 is an exploded, upper perspective view of the preferred wound-closing apparatus of the invention;

FIG. 2 is an exploded, lower perspective view of the preferred wound-closing apparatus of the invention;

FIG. 3 is a side elevational view of the fully assembled apparatus;

FIG. 4 is an end view of the fully assembled apparatus;

FIG. 5 is a side view in partial vertical section illustrating the base portion of the apparatus, with the force-exerting springs in the released position thereof;

FIG. 6 is a vertical sectional view taken along the line 6-6 of FIG. 5;

FIG. 7 is a vertical sectional view taken along the line 7-7 of FIG. 5;

FIG. 8 is a side view in partial vertical section illustrating the base portion of the apparatus, with the force-exerting springs in the cocked position thereof;

FIG. 9 is a vertical section view taken along the 9-9 of FIG. 8;

FIG. 10 is a vertical section view taken along the line 10-10 of FIG. 3;

FIG. 24 is a perspective view of a force-transmitting body of a wound closure apparatus designed for the closure of radial or brachial wounds;

FIG. 25 is a perspective view of an entire wound closure apparatus including the body of FIG. 24 and an elongated connection strap secured to the body;

FIG. 26 is a perspective view of the wound closure apparatus of FIG. 25, but shown as it would be connected to a wrist or upper arm of a patient;

DETAILED DESCRIPTION OF THE PREFERRED EMBODIMENT

Figure 11:
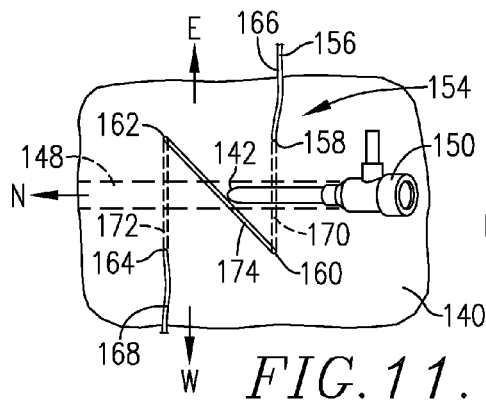
FIG. 11 is a top view illustrating a catheter sheath positioned within a wound attendant to a vascular procedure, and further illustrating the first step in the preferred method of the invention wherein a Z-shaped stitch has been created with a suture in the patient's tissue.

The Preferred Wound Closure Apparatus of FIGS. 1-23

Turning now to the drawings, apparatus 30 operable to close a wound in a patient's tissue is illustrated in FIGS. 1-4. The apparatus 30 is particularly designed for closure of wounds attendant to an endovascular (i.e., arterial or venous) intervention involving, e.g., a femoral artery puncture where the wound presents an insertion site, an elongated, obliquely oriented tract extending into the patient's tissue and communicating with the insertion site and an arteriotomy. Broadly speaking, the apparatus 30 includes a force-transmitting body 32 having a force-exerting assembly 34 together with a removable cover or "hat" 36.

As used herein, terms such as "upper" and "lower," "top and "bottom," and "downwardly" and "upwardly" and the like are used for convenience and because of the fact that the apparatus 30 is normally positioned in an upright orientation on a patient with the cover 36 being directly above the body 32. However, if the apparatus 30 were to be placed in a different orientation (e.g., sideways) the cover 36 would nonetheless be deemed to be above the body 32, and the above terms are intended to embrace all such different orientations.

In more detail, the body 32 is of rigid unitary construction and is formed of an appropriate synthetic resin material. The body 32 has first and second, axially aligned cup-like sections 38 and 40, each with an arcuate, upstanding sidewall 42, 44, a bifurcated, rectilinear end wall 46, 48, and a bottom wall 50, 52 serving to interconnect the section 38, 40. A pair of grooves 54 and 56 are provided between each of the end wall bifurcations as best seen in FIG. 2. The bottom walls 50, 52 are configured to present first and second substantially flat and coplanar force-transmitting sections 58 and 60; it will be observed that the area of section 58 is smaller than that of section 60, and this is important for purposes to be described.

A protruding, downwardly extending segment 62 bridges and is integral with the bottom walls 50, 52 and presents a lowermost, generally T-shaped third force-transmitting surface 64 which bridges the sections 38 and 40. The surface 64 presents an elongated, obliquely oriented and progressively tapered segment 66 extending from the end of bottom wall 52 to a point below bottom wall 50. Another surface segment 68 is generally transverse to the elongated segment 66 and is substantially centrally located below bottom wall 50. The segment 62 further includes a generally U-shaped sidewall 70 extending downwardly from the bottom walls 50, 52 of the sections 38, 40.

It will be appreciated that the body 32 presents an overall force-transmitting surface 72 made up of the force-transmitting sections 58, 60, 64, and 68. This surface 72 is three-dimensionally asymmetric owing to the fact that the area of first surface section 58 is less than that of the second surface section 60 (so that the overall surface 72 is asymmetric in a fore-and-aft direction), and because of the fact that the inclined surface segment 66 and transverse surface segment 68 are positioned below the first and second sections 58, 60 (so that the overall surface 72 is asymmetric in a vertical direction). Moreover, the inclined segment 66 provides an increasing and progressive force gradient from the second surface section 60 to the transverse segment 68.

The sections 38 and 40 are each equipped with an upstanding, slotted, tubular member 74 or 76 which extend upwardly from the upper surfaces of the corresponding bottom walls 50, 52. As best seen in FIGS. 5 and 8, an elongated, downwardly extending cylindrical opening 78 is formed in bottom wall 50 and protruding segment 62 directly beneath and coaxial with the tubular member 74. Likewise, a shorter, downwardly extending cylindrical opening 80 is provided directly beneath and coaxial with tubular member 76. Each of the openings 78, 80 has a plurality of elongated, upright, circumferentially spaced apart, inwardly extending, integral ribs 82.

The configuration of the tubular members 74, 76 is identical, and therefore only the construction of member 74 will be described in detail. Specifically, member 74 has an upstanding sidewall 84 with a pair of specially configured and opposed slots 86 formed therein. The sidewall 84 is reinforced by means of external gussets 88 and braces 90. Each slot 86 includes a lowermost, substantially frusto-circular portion 92, an intermediate upright portion 94, and an uppermost, inwardly extending lip portion 96.

The force-exerting assembly 34 generally includes a pair of identical, helically coiled springs 98, 100 respectively housed within a corresponding tubular member 74, 76 and supported therein by means of the adjacent upstanding ribs 82. The overall assembly 34 further includes an elongated, axially rotatable paddle-like operator 102, which extends fore and aft and is received by the opposed slots 86, so that the operator extends through and is supported by both of the tubular members 74, 76 and engages the springs 98, 100. The operator 102 is likewise formed of synthetic resin material and includes a central segment 104, a pair of identical, elongated, slotted, oval-shaped segments 106 and 108 on opposite sides of the central segment 104, and fore-and-aft segments 110, 112.

Referring to FIG. 5, it will be observed that the central segment 104 is cylindrical in configuration and has a central, peripheral, suture-receiving groove 114 formed therein. The oval segments 106, 108 are situated within the tubular members 74, 76 and have major axes 116 and transverse, minor axes 118 (FIG. 6). The fore end segment 110 has a rounded outer edge, whereas the corresponding aft end segment 112 has a recessed trailing edge. In this fashion, the operator 102 has an arrow-like shape along the length thereof.

The operator 102 serves to allow selective compression of the springs 98, 100 so as to maintain the springs in a cocked position as best seen in FIGS. 8 and 9. Upon 90° rotation of operator 102, the springs 98, 100 are released to a force-exerting position illustrated in FIGS. 5-7 and 10. In more detail, if it is desired to cock the springs 98, 100, the operator 102, in the FIG. 5-7 position where the major axes 116 are upright, is pressed downwardly through the upright portions 94 of the slots 86 until the bottom peripheries of the oval segments 106, 108 engage the bottoms of the frusto-circular portions 92. Thereupon, the operator 102 is rotated 90° in either direction so that the major axes 116 are substantially horizontal and the oval segments 106, 108 are captively retained by the frusto-circular portions 92. When it is desired to release the springs 98, 100, this operation is reversed, i.e., the operator 102 is rotated 90° until the major axes are again upright. The springs 98, 100 then urge the operator 102 upwardly to the FIGS. 5-7 position, with the lip portions 96 of the slots 86 serving to retain the operator 102 within the slots 86.

The cover 36 includes an uppermost wall 120 which is gently arcuate in cross-section and presents an upper surface 122 and a lower surface 124. A pair of depending, slotted tubular members 126, 128 extend from bottom surface 124 and are in alignment with the tubular members 74, 76. The members 126, 128 are identical, and therefore only member 126 will be described in detail. As best seen in FIGS. 1, 2, and 4, the member 126 includes a sidewall 130 with a pair of opposed slots 132. Each slot 132 includes an uppermost arcuate portion 134 and a substantially rectilinear portion 136. The tubular members 126, 128 are of slightly larger diameter than the corresponding tubular members 74, 76, allowing the cover 36 to be positioned over body 32 and pressed downwardly over the tubular members 74, 76 to assume the position depicted in FIGS. 3-4. It will be observed in this respect that the slots 86 of the tubular members 74, 76 are in substantial alignment with the slots 132 of the tubular members 126, 128.

Preferred Method of Use of the Wound Closure Apparatus of FIGS. 1-23

Figure 12:
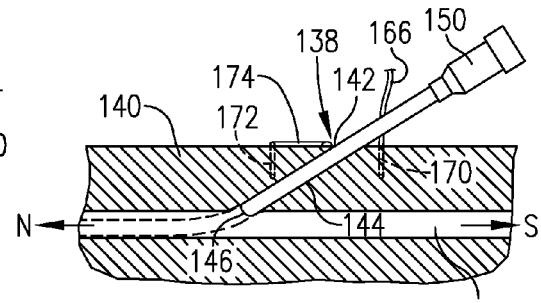
FIG. 12 is a sectional view of the wound, sheath, and suture depicted in FIG. 11.
Figure 13:
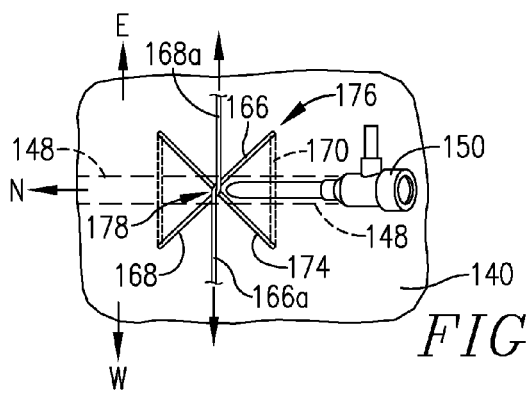
FIG. 13 is a top view illustrating the next step in the preferred method wherein the ends of the suture are tied to define an X-shaped stitch over the patient's skin.
Figure 14:
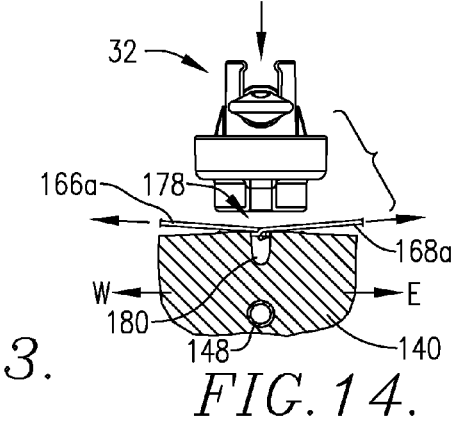
FIG. 14 is an end view in partial section illustrating the next step in the preferred method wherein the X-shaped stitch is tightened to invert the patient's skin adjacent the wound opening and the base of the apparatus is pressed downwardly over the stitch and wound opening.
Figure 15:
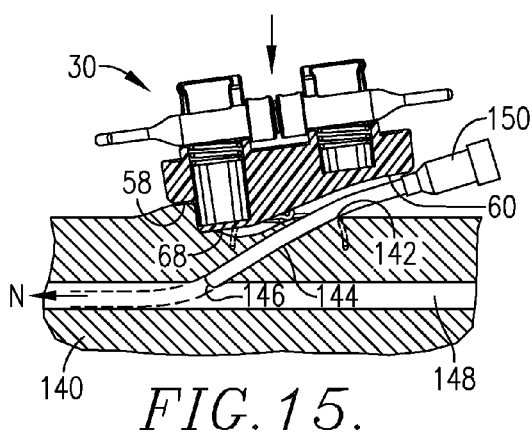
FIG. 15 is a sectional view of the steps depicted in FIG. 14.
Figure 16:
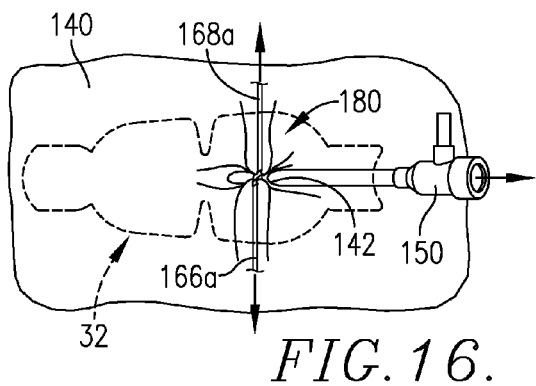
FIG. 16 is a top view of the steps illustrated in FIGS. 14 and 15, with the apparatus base illustrated in phantom and also showing withdrawal of the catheter sheath from the wound tract.
Figure 17:
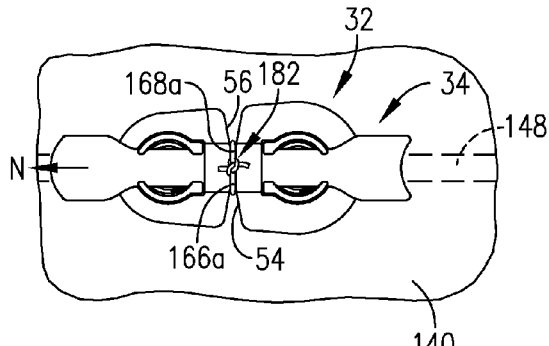
FIG. 17 is a top view of the next step of the method wherein the ends of the suture are passed around the rotatable operator forming a part of the apparatus base and knotted.
Figure 18:
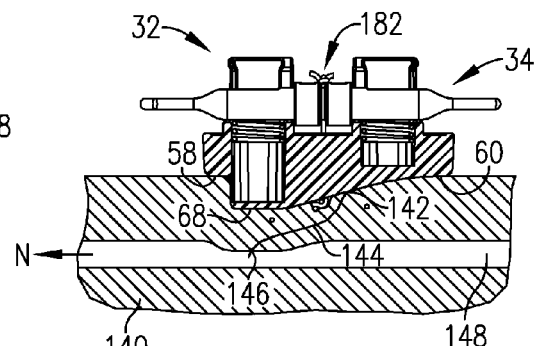
FIG. 18 is a sectional view illustrating the position of the apparatus base and operator after the tying and knotting step illustrated in FIG. 17.
Figures 19, 20:
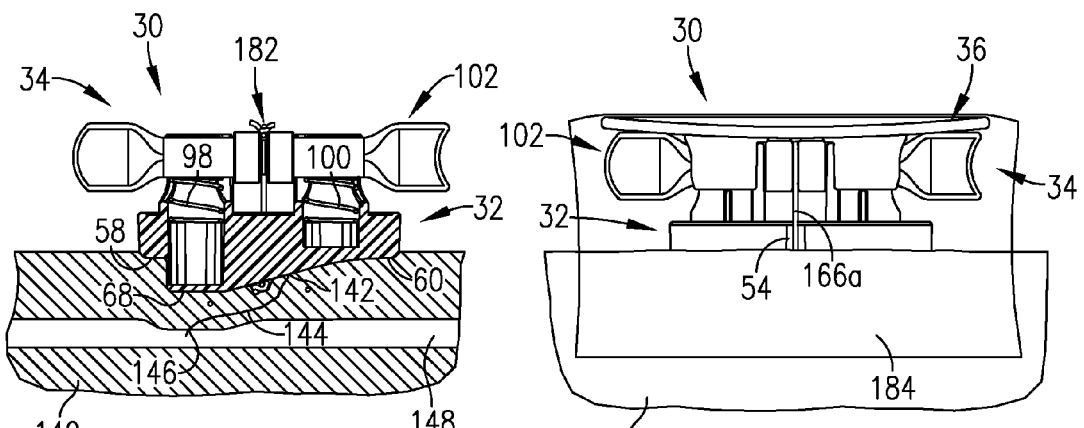
FIG. 19 is a view similar to that of FIG. 18, but illustrating the operator rotated to allow the force-exerting springs of the base to move from the cocked to the released position thereof so as to close the wound tract and reduce blood flow through the patient's artery adjacent the wound arteriotomy.
FIG. 20 is a side view of the installed apparatus with a cover secured to the base and with a stretch of adhesive passed over the cover and secured to the patient's tissue on opposite sides of the wound and apparatus.
Figure 21:
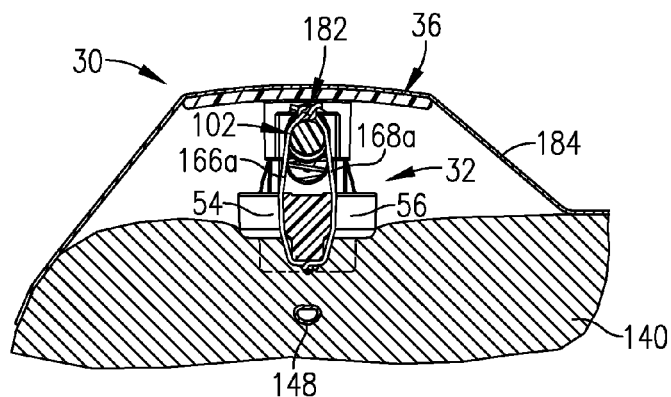
FIG. 21 is a vertical sectional view of the fully installed apparatus illustrated in FIG. 20.

The preferred method of using the apparatus 30 is depicted in FIGS. 11-23, in the context of the closure of a femoral artery puncture wound 138 (FIG. 12). It is to be understood, however, that the ensuing discussion is exemplary only, and that the invention can be used in virtually every type of endovascular arterial or venous intervention.

The wound 138 is in the groin tissue 140 of a patient and includes an insertion site 142, an elongated, obliquely extending tract 144 extending from insertion site 142 and terminating at an arteriotomy 146 in the femoral artery 148. A conventional catheter sheath 150 is positioned within the tract 144 in order to permit an endovascular procedure using a catheter (not shown). When the procedure is completed and the catheter removed, it is necessary to promptly close the wound 138 during removal of the sheath 150, while minimizing any blood loss and rendering the patient ambulatory in as short a period as possible.

In order to facilitate the description of the preferred wound closure technique, the direction towards the patient's heart is denominated as "north," whereas the direction leading away from the heart is denominated "south." Correspondingly, transverse directions are denominated as "east" and "west," respectively. Accordingly, it will be observed that the tract 144 extends from the insertion site 142 to the arteriotomy 146 in a generally northerly direction.

In the first step of the wound closure procedure, the endovascular physician creates a Z-stitch 154 (FIGS. 11-12) in the patient's tissue 140 by passing a suture 156 through an entrance 158 east of the artery 148 and south of insertion site 142, an exit 160 west of artery 148 and south of insertion site 142, an entrance 162 north of insertion site 142 and east of artery 148, and finally an exit 164. The end of the suture 156 adjacent entrance 158 is then clipped. The stitch 154 thus includes exterior suture stretches 166 and 168, embedded suture stretches 170 and 172 above artery 148 at a depth of less than about one-half inch, and an obliquely extending exterior stretch 174 extending between the exit 160 and entrance 162.

In the next step (FIG. 13), the exterior suture stretches 166 and 168 are crossed and interconnected by folding the stretches over each other, thereby creating an X-stitch 176 with a central suture fold 178, and with the free ends 166a, 168a of the exterior suture stretches 166, 168 extending westerly and easterly, respectively. Preferably, the suture fold 178 is positioned in very close proximity or over the insertion site 142.

The next step (FIGS. 14-18) requires two health care providers and generally involves tightening of the X-stitch 176 while the force-transmitting body 32 of apparatus 30 is positioned atop wound 138 with application of a downwardly directed force, and the sheath 150 is removed. In detail, one care provider grasps the free suture ends 166a, and 168a, and pulls these in an easterly and westerly direction, respectively. This serves to tighten the suture while inverting the patient's skin tissue, as illustrated by numeral 180, at the region of the insertion site 142. That is, uninvolved, parallel peripheral tissue is forced upwardly, while the central tissue adjacent the wound is pushed downwardly over the entire insertion site 142, tract 144, and arteriotomy 146. The inverted tissue in cross-section thus resembles an M in shape.

Once the skin is inverted, the second provider presses body 32 (which is in the spring-cocked position thereof) downwardly into the patient's tissue 140, while withdrawing the sheath 150. In particular, the body 32 is located in general north-south alignment with the artery 148, such that the force-transmitting surface sections 58 and 68 are above and north of insertion site 142 and arteriotomy 146, with the oblique section 64 over the suture fold 178, and with the rearmost portion of surface section 60 located south of the insertion site 142. As the body 32 is held in this position, the first provider, while still maintaining tension on the suture free ends 166a and 168a, pulls the ends upwardly through the body grooves 54 and over the central segment 104 of operator 102, and forms a secure knot 182 at the top surface of the segment 104. In this condition (see FIGS. 17-18) the artery upstream of arteriotomy 146 is partially closed, whereas tract 144 and arteriotomy 146 are fully closed.

In preferred practice, the suture ends 166a, 168a are pulled upwardly while avoiding any twisting prior to formation of the knot 182. This avoids reduction in the burst strength of the suture ends. That is, if the ends are twisted prior to knotting, the burst strength of the suture ends is reduced and can induce premature failure of apparatus 30.

In order to establish and maintain a substantially constant and time-invariant wound closure force, the operator 102 is rotated 90° so that the springs 98, 100 are released to their force-exerting positions (FIGS. 5-7 and 19). This serves to maintain the suture 156 in tension so as to firmly draw the body 32 into the wound-closure position while also maintaining a substantially even force based upon the strengths of the springs 98, 100. Preferably, the tensile force exerted on the suture 156 is slightly below the burst strength thereof; thus, the tensile force on suture 156 should typically be 10-15% less than the suture burst strength.

Next, the cover 36 is positioned atop body 32 by pressing the tubular members 126, 128 over the tubular member 74, 76 until the cover is firmly seated. At this point, a length of wide adhesive material 184 (e.g., 6×8 inches) is placed over the cover 36 with the ends of the material 184 being pulled downwardly and adhesively attached to the patient's tissue at east and west and north and south locations, respectively. This material 184 may be stretchable or non-stretchable, and if desired may be breathable. Placement of the material 184 serves to exert a secondary force through the body 32, in addition to that exerted by the springs 98, 100, while also stabilizing the apparatus 30 on the patient. Advantageously, the height of the apparatus 30 above insertion site 142 divided by the maximum east-west transverse dimension of the force-transmitting surface 72 is greater than 1. With this ratio, the vertical component of the force generated by the material 184 is increased, causing additional force to be applied over the entirety of the wound.

As finally positioned, the apparatus 30 creates targeted, asymmetric tissue pressures from north to south. At the north, a larger, non-occlusive pressure is applied upstream of the arteriotomy 146 in order to lower the patient's blood pressure and blood flow at the downstream arteriotomy. The transverse surface segment 68, positioned directly above the arteriotomy 146, closely mimics a properly executed two-handed manual wound closure. The lesser tissue pressures created south of the arteriotomy 146, owing to the decreasing force gradient generated through the oblique section 66, and the greater surface area of southernmost section 60, also are similar to such manual closure.

Figure 22:
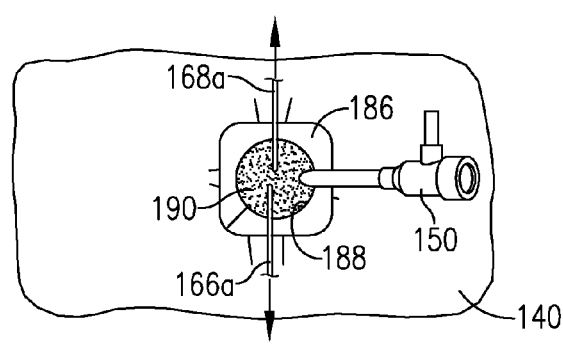
FIG. 22 is a top view of a preferred additional method step wherein a dam is placed around the wound opening and the sheath, and a hemostatic powder is deposited within the confines of the dam and over the wound opening.

FIG. 22 depicts another preferred aspect of the invention, namely the use of a compressible dam 186 having a central opening 188 over the wound. In particular, the dam is placed in surrounding relationship to the insertion site 142 and a hemostatic powder 190 is sprinkled into the opening 188 (about 0.3 g). This procedure is carried out prior to tensioning of the suture free ends 166a, 168a, and placement of the apparatus 30 on the wound site, as previously described. Of course, the dam remains in place during the entire closure sequence, and is then removed after closure. The hemostatic powder 190 may be a cationic surfactant combined with a strong acid cation exchange resin, or a potassium ferrate/strong acid cation exchange resin. Preferably, the powder 190 is of the type described in U.S. Pat. No. 6,187,347. In another embodiment, a sheet of exudate-absorbing woven or nonwoven hemostatic material (such as oxidized cellulose or chitosan) may be used in lieu of or in addition to the powder 190.

Figure 23:
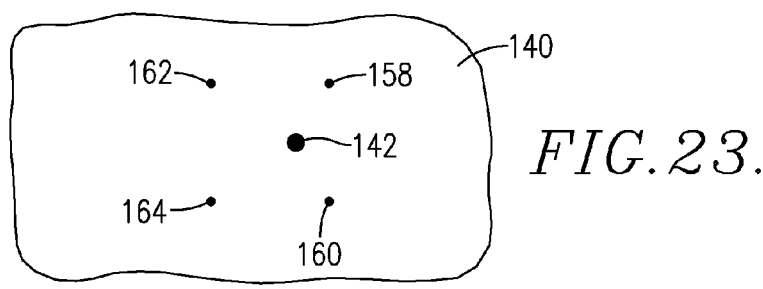
FIG. 23 is a top view of the condition of the patient's tissue after wound closure and with the patient ambulatory.
Figure 27:
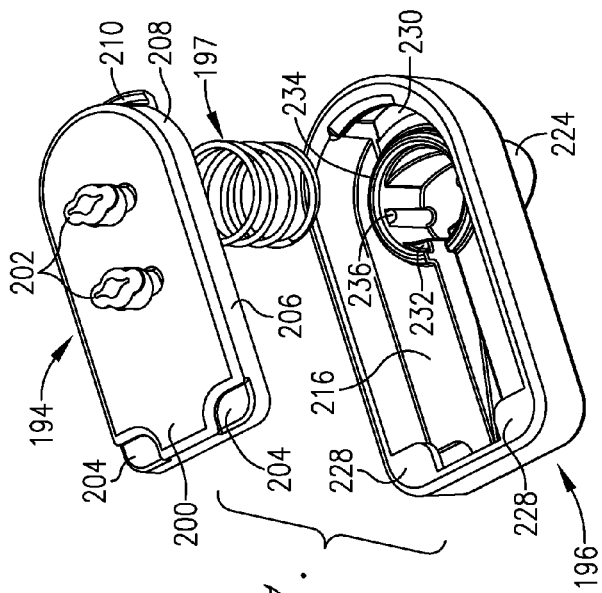
FIG. 27 is a top perspective exploded view of the force-transmitting body of FIG. 24.
Figure 28:
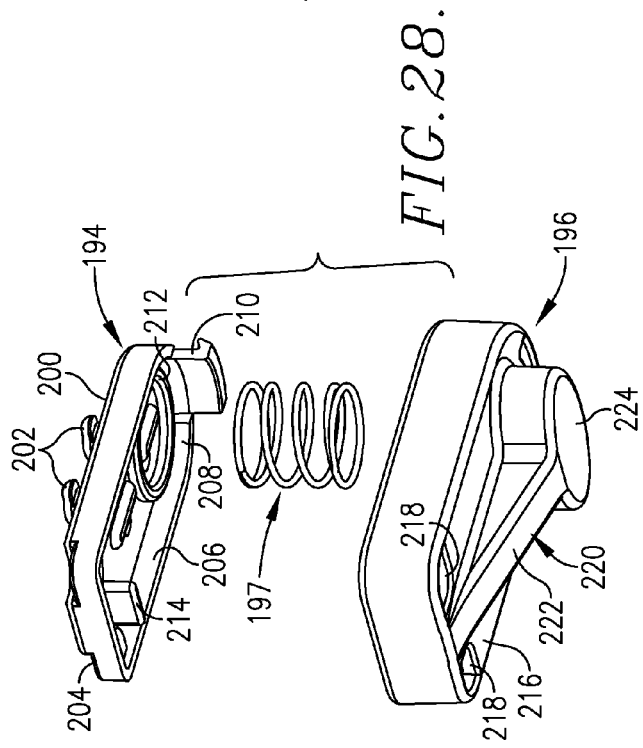
FIG. 28 is a bottom perspective exploded view of the force-transmitting body of FIG. 24.
Figure 29:
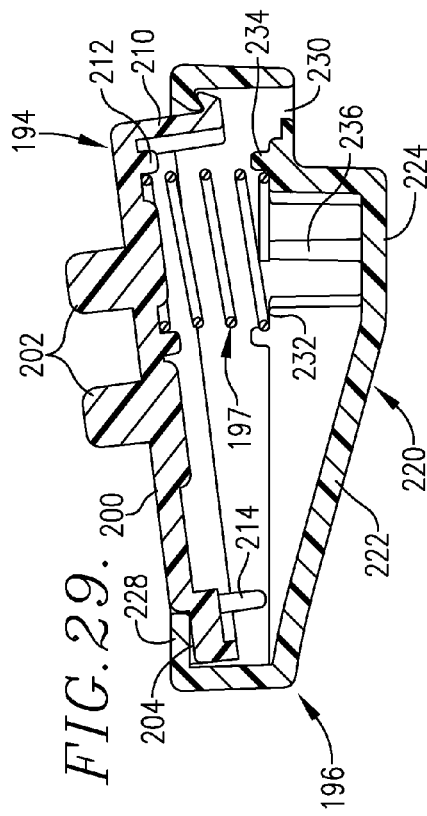
FIG. 29 is a vertical sectional view of the force-transmitting body of FIG. 24, illustrated in its relaxed condition.
Figure 30:
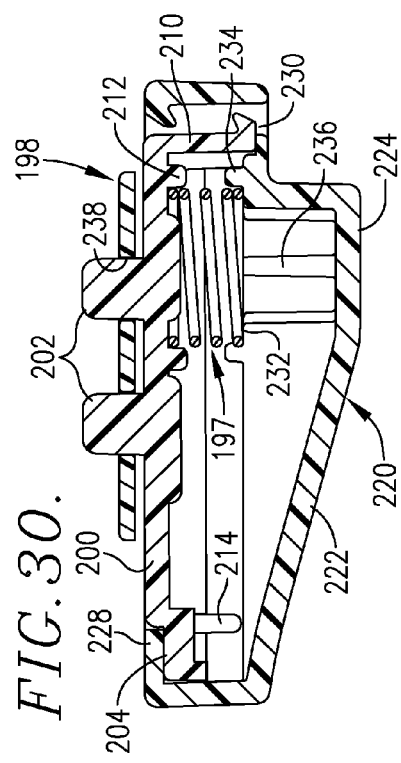
FIG. 30 is a vertical sectional view similar to that of FIG. 29, but illustrating the body in its force-transmitting position.

FIG. 23 illustrates the condition of the wound 138 at the completion of wound closure. After the appropriate closure time, the knotted suture 156 is cut and the apparatus 30 is removed from the wound 138. It will be seen that the insertion site 142 is closed (clotted) with the suture openings likewise closed. If desired or needed, a hemostatic/antiseptic powder can be sprinkled over the insertion site and the suture openings to help prevent infections and inhibit oozing. Normally, no dressing is required, and the loose powder is merely brushed off the wound site.

A significant advantage of the invention is that TTAs are substantially reduced. In the case of diagnostic procedures, TTAs on the order of 60 minutes are common, and with more complex interventional procedures, TTAs of 120 minutes are typical. In a pre-clinical study involving 100 patients with interventional procedures up to 12 Fr, the preferred apparatus of the invention closed the patients' wounds with no complications and TTAs of less than 120 minutes The invention also is useful with seriously obese patients. With such patients, the panniculus descends to the femoral insertion site, interfering with normal deployment of closure devices. This restricts the space around the wound and the ability of the healthcare professional to properly apply manual closure pressure. However, in the present invention, pre-compression of the springs 98, 100 and latching them with the operator 102 allows the device to be aligned over the wound and the knot 182 tied. Thereupon, the operator 102 is rotated to release the springs, and the material 184 is applied.

The Preferred Wound Closure Apparatus of FIGS. 24-30

As will be readily appreciated, the apparatus of FIGS. 1-23 is primarily designed for the closure of femoral arterial wounds. The apparatus of FIGS. 24-30 is similar in design and use to the first embodiment, but is specifically designed for the closure of a significantly smaller radial or brachial arterial wounds respectively adjacent the wrist and bicep areas of the patient. Such interventions create relatively small wounds, but nevertheless are of the same character as the wound 138 described above, i.e., the wounds (not shown) have insertion sites and elongated, obliquely extending (normally about 45°) tracts extending from the insertion sites and terminating at arteriotomies in the brachial or radial arteries. These wounds also extend substantially from south to north, as explained previously, generally along the lengths of the corresponding arteries.

FIGS. 24-30 illustrate a wound closure apparatus broadly referred to by numeral 192, including an upper force-exerting member 194, a lower force-transmitting member 196, an intermediate compression spring 197, and an attachment band 198.

In more detail, the force-exerting member 194 is of integrally formed synthetic resin construction, and includes a top panel 200 having a pair of upstanding, spaced apart strap attachment protrusions or cleats 202, a pair of butt end indentations 204, and a depending peripheral sidewall 206. The rounded end sidewall 208 includes a depending, somewhat L-shaped, resilient locking tongue 210. The underside of top panel 200 includes an arcuate spring retainer 212 and a depending stop wall 214.

The force-transmitting member 196 is also an integrally molded, synthetic resin body, and includes a bottom panel 216 having a pair of spaced apart butt end openings 218 and a somewhat T-shaped, depending, force-transmitting surface 220. The surface 220 presents an elongated, obliquely oriented and progressively tapered segment 222 depending from panel 216, with an elongated, transversely oriented segment 224. It will be appreciated that the surface 220 is in many respects similar to the previously described surface 64 of the first embodiment, but of course is smaller in overall size. The upper surface of panel 216 includes an upstanding peripheral sidewall 226 with a pair of butt end projections 228 in alignment with previously described openings 218, and with a recess 230 formed in the rounded end of the sidewall 226. Additionally, a spring retainer well 232 is provided above the transverse segment 224 and has an upper lip 234 and recessed spring-supporting structure 236.

Compression spring 197 is itself conventional and is sized so that one end thereof fits within retain well 232, whereas the other end is seated within spring retainer 212. Likewise, the strap 198 is formed of conventional, somewhat stretchable synthetic resin and is of a length to extend around a patient's bicep or wrist. As illustrated, the strap 198 has a series of openings 238 along the length thereof, which are provided in side-by-side pairs and are sized to fit over the cleats 202.

The apparatus 192 is assembled by first securing the inboard end of strap 198 to the cleats 202, followed by placement of one end of spring 197 within well 232. Thereupon, the member 194 is secured to the member 196 by first positioning the indentations 204 beneath the projections 228 and pressing the member 194 downwardly until the locking tongue 210 seats within the recess 230; in some instances, it may be necessary to exert a slight inwardly directed force against the tongue 210 to be sure that the tongue clears the upper edge of the sidewall 226. As assembled, it will be appreciated that the member 194 is essentially nested within the member 196, with the spring 197 serving to urge the two members apart, but permitting relative movement between the members 194, 196 against the bias of spring 197. In preferred practice, the ultimate user does not assemble the apparatus 192, but rather it is sold in an assembled condition. Preferred Method of Use of the Wound Closure Apparatus of FIGS. 24-30

In the use of apparatus 192, an attendant first positions the assembled apparatus over the radial or brachial wound site, with the T-shaped force-transmitting surface 220 in covering opposition and in spanning relationship to the wound. Next, the attendant grasps the free end of strap 198 and pulls it around the patient's wrist or upper arm with slight stretching and tensioning of the strap, and then snaps an adjacent pair of the strap openings 238 over the cleats 202 atop the attached end of the strap. This generates a compressive force serving to compress spring 197 and create the desired wound closure force. As before, the apparatus 192 is oriented in a general north-south alignment with the radial or brachial artery, with the transverse segment 224 north of the insertion site and arteriotomy, and therefore closest to the patient's heart, and with the oblique segment 222 extending in a southerly direction away from the segment 224 and the patient's heart. Of course, the apparatus 192 is attached in such manner as to generate the required degree of wound-closing force.

Thus, the apparatus 192 is designed to apply a larger, non-occlusive pressure upstream of the arteriotomy in order to lower the patient's blood pressure and blood flow at the downstream arteriotomy. Hence, the greatest pressure and force is applied closest to the patient's heart, with a decreasing force gradient owing to the presence of the oblique segment 222 away from the patient's heart. The overall force profile provided by the apparatus 192 is essentially identical, except in magnitude, to the force profile exerted by the previously described apparatus 30, and closely mimics a properly executed manual wound closure, while not requiring the presence of a medical attendant throughout the closure.

As indicated, the apparatus 192 is especially designed for use in closing radial artery (left or right) wounds, as well as brachial artery wounds. To this end, the apparatus 192 is sized for this purpose and generates sufficient force for rapid wound closure. An advantage of the apparatus 192 is that it does not make use of any sutures, thus simplifying the installation of the apparatus.

We claim:

1. A method of closing a wound in a patient's tissue, said wound presenting an insertion site opening and an elongated, obliquely oriented tract extending into said patient's tissue and in communication with said opening, said method comprising the steps of:
    positioning a body in a wound-closing position proximal to the patient's skin and adjacent and in spanning relationship to said wound, said body having an elongated force-transmitting surface having a length greater than the width thereof and positioned in general axial alignment with said tract, at least a portion of said elongated force-transmitting being tapered along the length thereof,
    said positioning step comprising the steps of using a strap to secure said body in said wound closing position; and
    exerting a force through said force-transmitting surface in order to close the wound, said force having different magnitudes of pressure at different locations along the length of said force-transmitting surface,
    said force being greatest adjacent one end of said force-transmitting surface closest to the patient's heart, and decreasing along the length of the force-transmitting surface away from the patient's heart.

2. The method of claim 1, including the step of exerting said force substantially invariantly over a period of time to close said wound.

3. The method of claim 1, said wound tract communicating with an opening formed in a vascular vessel within the patient's tissue, said body and force-exerting assembly cooperatively configured to reduce the blood pressure within and downstream of said vascular vessel.

4. The method of claim 1, said force-transmitting surface being three-dimensionally asymmetric.

5. The method of claim 1, said force-exerting assembly having a mechanism including a shiftable component for generating a mechanically-derived force through said force-transmitting surface.

6. The method of claim 5, said mechanism comprising biasing structure including at least one spring.

7. The method of claim 1, said wound tract communicating with an opening formed in a vascular vessel within the patient's tissue, said body and force-exerting assembly cooperatively configured to reduce the blood flow within said vascular vessel.

8. Apparatus operable to close a wound in a patient's tissue, said wound presenting an insertion site and an elongated, obliquely oriented tract extending into the patient's tissue and in communication with said insertion site, said apparatus comprising:
- a body having an elongated force-transmitting surface having a length greater than the width thereof, at least a portion of said elongated force-transmitting being tapered along the length thereof, said body operable to be placed in an external wound-closing position with said force-transmitting surface proximal to the patient's skin, adjacent and in spanning relationship to said wound, and also in general axial alignment with said tract,
- said force-transmitting surface comprising first and second surface sections having different force-transmitting areas, respectively, said first and second surface sections being substantially coplanar, there being a third, generally T-shaped surface section bridging said first and second surface sections and presenting an elongated segment and a segment transverse to the elongated segment, said elongated segment including said tapered portion of the force-transmitting surface;
- a force-exerting assembly coupled with said body and operable to exert forces of different magnitudes at different locations along the length of said force-transmitting surface in order to close the wound; and
- a strap operable to attach said body to a patient with said force-transmitting surface adjacent said wound.

9. The apparatus of claim 8, said body operable to be placed proximal to the patient's skin with one end of said force-transmitting surface closest to the patient's heart, and decreasing along the length of the force-transmitting surface away from the patient's heart, in order to apply a greater pressure adjacent said one end of the force-transmitting surface.

10. The apparatus of claim 8, said force-transmitting surface being three-dimensionally asymmetric.

11. The apparatus of claim 8, said force-exerting assembly having a mechanism including a shiftable component for generating a mechanically-derived force through said force-transmitting surface.

12. The apparatus of claim 11, said mechanism comprising biasing structure including at least one spring.

13. The apparatus of claim 8, said wound tract communicating with an opening formed in a vascular vessel within the patient's tissue, said body and force-exerting assembly cooperatively configured to reduce the blood flow within said vascular vessel.

14. The apparatus of claim 8, said different magnitude mechanically-derived forces being substantially invariantly exerted over a period of time to close said wound.

15. The apparatus of claim 8, said strap including a plurality of attachment openings along the length thereof.

* * * * *